United States Patent [19]
Liu et al.

[11] Patent Number: 5,572,037
[45] Date of Patent: Nov. 5, 1996

[54] DIGITAL IMAGING USING A SCANNING MIRROR APPARATUS

[75] Inventors: Hong Liu, Worcester; Andrew Karellas, Auburn, both of Mass.

[73] Assignee: University of Massachusetts Medical Center, Worcester, Mass.

[21] Appl. No.: 383,411

[22] Filed: Feb. 3, 1995

[51] Int. Cl.[6] .................. G01N 23/04; G01N 21/63; G01T 1/24; H01L 27/00
[52] U.S. Cl. .................. 250/483.1; 250/487.1; 250/332; 250/363.02; 250/334; 250/360.1; 250/370.09; 250/370.08; 250/370.1; 250/371; 378/62; 378/146
[58] Field of Search .................. 250/483.1, 487.1, 250/363.01, 363.02, 370.08, 370.09, 370.1, 371, 332, 334, 363.02, 359.1, 360.1; 378/62, 63, 70, 146

[56] References Cited

U.S. PATENT DOCUMENTS

| | | | |
|---|---|---|---|
| 3,634,695 | 1/1972 | Barringer | 250/550 |
| 3,771,124 | 11/1973 | McMahon | 382/127 |
| 3,792,273 | 2/1974 | Bergstedt | 250/366 |
| 4,012,636 | 3/1977 | Engdahl et al. | 250/363.02 |
| 4,135,096 | 1/1979 | Giordano | 364/413 |
| 4,442,538 | 4/1979 | Haendale | 378/146 |
| 4,504,859 | 3/1985 | Grady et al. | |
| 4,544,949 | 10/1985 | Kurihara | |
| 4,789,782 | 12/1988 | Ohara | |
| 4,816,676 | 3/1989 | Aagano | |
| 4,896,344 | 1/1990 | Grady et al. | |
| 5,138,167 | 8/1992 | Barnes | 250/370.01 |
| 5,138,642 | 8/1992 | McCroskey et al. | 378/19 |
| 5,233,639 | 8/1993 | Marks | 378/42 |
| 5,365,562 | 11/1994 | Toker | 378/62 |
| 5,412,705 | 5/1995 | Snoeren et al. | 250/487.1 |
| 5,440,426 | 8/1995 | Sandstrom | 359/559 |
| 5,452,721 | 9/1995 | Hacker | 250/363.02 |
| 5,453,618 | 9/1995 | Sutton et al. | 334/334 |

*Primary Examiner*—Constantine Hannaher
*Assistant Examiner*—Virgil Orlando Tyler
*Attorney, Agent, or Firm*—Fish & Richardson P.C.

[57] ABSTRACT

Method and apparatus for generating a large-field, high-resolution digital image of an object by sequentially generating multiple optical scenes representative of different portions of the object, and then sequentially directing each optical scene onto an optical detector to generate multiple sub-images of the different portions of the object. Each scene is induced using a separate X-ray sub-beam, each of which is generated by spatially filtering a portion of an incident X-ray field with a spatial filter moving in concert with the scene-directing device. Once generated, the sub-images are combined to form the large-field, high-resolution image.

20 Claims, 7 Drawing Sheets

DIGITAL IMAGING USING A SCANNING MIRROR APPARATUS

BACKGROUND

This invention relates to imaging systems using electronic detectors, such as charge-coupled devices (CCDs).

CCDs containing multi-pixel arrays are typically used in imaging systems to detect optical radiation and generate electronic images. When exposed to an optical field, each pixel in the array generates a light-induced electronic charge related to the intensity of the field. The charges of the array are then digitized and processed to generate the resultant digital image. Image resolution is dictated by the parameters of the CCD's pixel array; current high-end CCDs typically include 2048×2048-pixel arrays having dimensions of about 5 cm×5 cm, with each pixel having a dimension of about 25 µm×25 µm. CCDs having high spatial resolution are particularly useful, for example, in fields such as mammography and radiography, where sizes of the smallest lesions are typically between about 0.2 and 0.4 $mm^2$.

While CCDs represent effective means for generating digital electronic images, they are expensive and have limited spatial resolution and detector area. In particular, CCDs fabricated to detect large-area images with high spatial resolution are prohibitively expensive as the cost of a CCD scales non-linearly with the size of the pixel array. Moreover, the probability of defects within the pixel array is greatly increased for large-area CCDs. Lower-cost CCDs with adequate spatial resolution are commercially available, although the detector areas of these devices are often too small to effectively image a region of interest.

There is a need, therefore, to generate detection methods and devices for producing large-area, high-resolution images at reasonable costs. Imaging techniques involving the combination of images detected with multiple CCDs, each having high spatial resolution but a small effective area, have been taught in the prior art. For instance, U.S. Pat. No. 5,138,642 describes an X-ray system that generates multiple segments of an optical image; each segment is delivered to a separate CCD detector. The light-induced signals from each detector are then combined to produce an image containing each of the segments.

SUMMARY OF THE INVENTION

In general, in one aspect, the invention features a method for generating a large-field, high-resolution digital image of an object. The method includes the steps of: (a) generating a first optical scene representative of a first portion of the object, and then directing the first optical scene onto an optical detector to generate a sub-image of the first portion of the object; (b) generating a second optical scene representative of a second portion of the object, and then directing the second optical scene onto the optical detector to generate a sub-image of the second portion of the object; and, (c) combining all sub-images to form a large-field, high-resolution image of the object.

The method may further include, prior to step (c), the steps of generating third and fourth optical scenes representative of, respectively, third and fourth portions of the object, and then sequentially directing these scenes onto the optical detector to generate sub-images of the third and fourth portions of the object. In this case, for example, step (c) includes combining the first, second, third, and fourth sub-images to form the large-field, high-resolution image.

In preferred embodiments, the optical scene is directed onto an optical detector by a reflecting assembly. The reflecting assembly may be "scanned" (i.e., linearly translated or radially rotated) once the sub-image corresponding to the first optical scene is generated; this allows an additional optical scene to be directed onto the same optical detector. During scanning, the reflecting assembly is preferably rotated radially about a central axis, or longitudinally translated, to sequentially direct each optical scene onto the detector. Preferably, the reflecting assembly includes a first and second mirror, with the first mirror configured to receive and reflect the optical scene off the second mirror and onto the optical detector. In another embodiment, the reflecting assembly has a single mirror positioned to reflect the optical scene onto the optical detector. In this case, the mirror assembly is surrounded by other mirrors configured to receive and reflect the scene onto the rotatable (or translatable) mirror. In still other embodiments, a prism may be used in place of any of the mirrors. Preferably, in all cases, the directing step further includes the step of focussing the optical scene onto the optical detector with an imaging system (e.g., a lens or series of lenses).

In other preferred embodiments, prior to the generating step, each of steps (a) and (b) includes spatially filtering first and second portions of an incident X-ray field to generate first and second X-ray sub-fields, and then projecting the first and second X-ray sub-fields (i) through the first and second portions of the object, and then (ii) through an X-ray-to-optical conversion screen to produce the first and second optical scenes. The step of spatial filtering includes positioning an opening of an X-ray-attenuating filter along the portion of the incident X-ray field in order to produce an X-ray field having a reduced spatial profile.

Once the sub-image corresponding to the optical scene is generated, the spatial filter is scanned and re-positioned to filter a second portion of the incident X-ray field. During the scanning step, the spatial filter may be rotated about a central axis to sequentially spatially filter portions of the incident X-ray field. Alternatively, the filter may include openings spaced in a linear fashion. In this case, the filter is longitudinally translated to sequentially spatially filter portions of the incident X-ray field. Preferably, in all cases, scanning of the spatial filter is coordinated with the scanning of the reflecting assembly, allowing these two devices to move in concert. For instance, in a preferred embodiment, the scanning of the spatial filter and the reflecting assembly are coordinated so that following step (a), the spatial filter and mirror assembly are simultaneously rotated radially along the same central axis, with the opening of the spatial filter positioned to filter a second portion of the incident X-ray field, and the reflecting assembly positioned to direct a second optical scene onto the optical detector. In this case, between steps (a) and (b), the spatial filter and mirror assembly may be simultaneously rotated about 90° along the same central axis.

In other preferred embodiments, the optical detector is a CCD including a 512×512, 1024×1024, or a 2048×2048-pixel array. CCDs having larger or smaller pixel arrays may also be used.

In still other preferred embodiments, step (c), i.e., the "combining" step, is performed on a computer using a computer algorithm. The algorithm allows the computer to perform the steps of (i) adjusting the two-dimensional array of points of each sub-image so that, when combined, each sub-image is representative of a separate portion of the object; and (ii) combining the adjusted two-dimensional arrays of points to form the resultant complete image of the object.

In another aspect, the invention features an apparatus for generating a large-field, high-resolution image of an object. The apparatus includes a means for generating optical scenes representative of at least two spatially separate portions of the object; a scanning and reflecting assembly configured to sequentially receive and then direct the optical scenes onto an optical detector to generate a sub-image for each optical scene; and, electronics (e.g., a computer) for combining the sub-images together to at least partially form the large-field, high-resolution image of the object.

The inventions have many advantages. For example, the method allows rapid generation of high-quality images, such as those images taken during radiography or mammography, which can be used to detect with high accuracy lesions and tumors in patients. By generating and then combining multiple electronic sub-images to form a complete image, the method allows production of large-area, high-resolution images using a single, commercially available, small-area detector. Because the cost of CCD detectors scales disproportionately with the detector area, this method allows generation of high-quality images at a relatively low cost. Additionally, by using two detectors to form two sub-images, and then recombining the sub-images to form a single image, the method allows generation of very high-resolution images with relatively low-end, low-cost detectors. This allows, for example, detection of small-scale lesions which may otherwise not be resolved using conventional detecting methods.

DETAILED DESCRIPTION OF THE DRAWINGS

Figure 1:
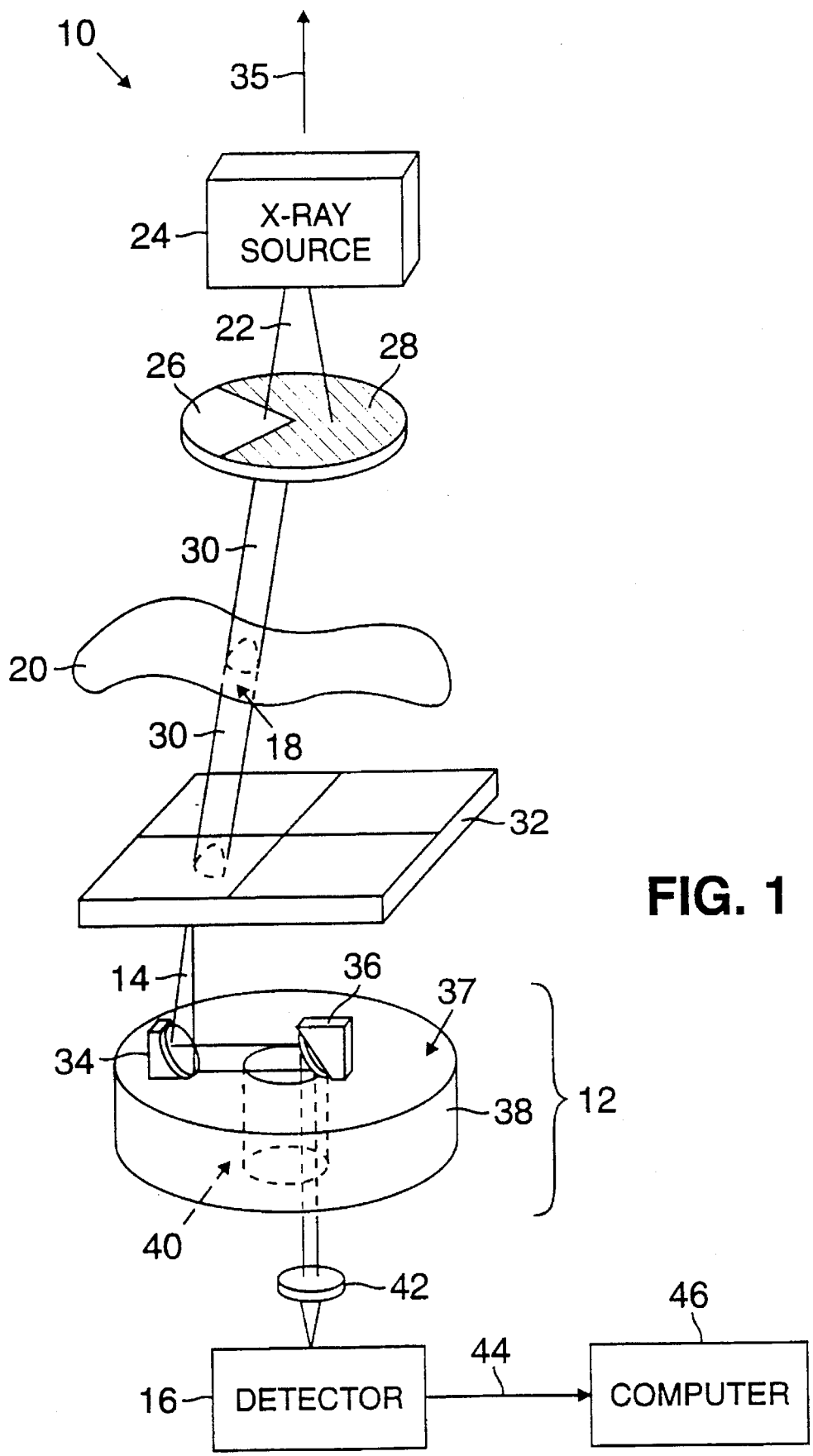
FIG. 1 is a perspective view of a scanning mirror apparatus according to the invention, which is used in combination with an X-ray source and filter wheel to generate a large-area, high-resolution image of an object.

Referring first to FIGS. 1 and 2A–2D, a digital imaging system 10 includes a reflecting assembly 12 which collects and steers an X-ray-induced optical scene 14 through an imaging system 42 and onto a detector 16. The scene is generated by passing an X-ray beam 22 from an X-ray source 24 through an open portion 26 of a rotating filter wheel 28 composed primarily of an X-ray-attenuating material (e.g., lead or a lead-based alloy) to generate an X-ray sub-beam 30. This sub-beam 30 has a spatial profile that represents one portion, e.g., one quadrant of X-ray beam 22. The sub-beam is then passed through a portion 18 of an object 20, which may be, for example, a human tissue. The incident X-ray sub-beam 30 is modulated as it passes through the object to produce a modulated X-ray sub-beam 30' which strikes a portion of an X-ray-to-optical conversion device 32, such as a luminescing (i.e., phosphoresing or fluorescing) screen, to generate the optical scene 14. Other image intensifiers known in the art, such as flat-panel or electrostatic intensifiers, may be used in place of the luminescing screen to generate the optical scene.

A pair of mirrors 34, 36 positioned on a surface 37 of a rotating mount 38 steer and collect the scene 14. To collect the optical scene, the first mirror 34 is positioned and angled with respect to the irradiated portion of the X-ray-to-optical conversion device 32 to reflect the scene 14 onto the surface of the second mirror 36. This optic is aligned along the central axis of the system, indicated in FIG. 1 by the arrow 35, and is positioned and angled above an opening 40 in the rotating mount 38. Optical scene 14 is reflected by the second mirror 36 through the opening 40 onto an imaging optical system 42, shown in FIG. 1 as a lens, where it is focussed onto the surface of the detector 16. The imaging system may be aligned and configured to magnify or demagnify the scene so that the optically active region of the detector is fully exposed. Although a single lens is shown, it is understood that imaging systems containing multiple optical components, such as reflective or refractive optics, may also be used. Detector 16 (e.g., a CCD) generates an electronic image corresponding to the optical scene 14, which is sent along line 44 to a computer 46 for display and analysis.

Filter wheel 28 rotates about the central axis 35 to generate multiple X-ray sub-beams for imaging. Mount 38 rotates about the same axis, preferably at the same rotational rate, to sequentially image the X-ray-induced optical scenes onto the detector 16, thereby forming multiple sub-images. These components can be rotated, for example, using standard motor-driven translational stages.

Because both the filter wheel 28 and the mount 38 may require openings in their respective centers to pass X-ray and optical fields, rotation is preferably driven by means coupled to the outer perimeter of these devices. For example, for filters and mounts having circular cross sections, the outer perimeter of these devices may include teeth configured to match external gears. In this case, rotation is driven by rotating the external gears about a separate axis. Other conventional means for rotation, such as belt-driven or magnetically coupled means, may also be used.

Once generated, each sub-image is sequentially digitized and stored in a computer 46, such as in a buffer or memory. When all sub-images are detected and stored, the complete image of the region of interest of the object 20 is determined by recombining the sub-images.

In addition, in order to increase the spatial resolution of the system, the digital imaging system 10 may be translated by a fraction of a pixel after one portion 18 of the object is imaged. This generates an additional sub-image, having a shifted pixel structure, for the same portion of the object. Eight sub-images, for example, would be generated for the four portions of the object. Recombination of each sub-image using this method results in an image having even higher spatial resolution than the image produced using a single sub-image for each portion.

In general, images are recombined using standard algorithms known in the art. Because each sub-image is "pixelized," i e. contains a two-dimensional array of points according to the pixel array of the detector, recombination may be accomplished by shifting the pixels of each sub-image by a predetermined number of pixels, and then adding the modified sub-images to form the complete image.

Figure 7A:
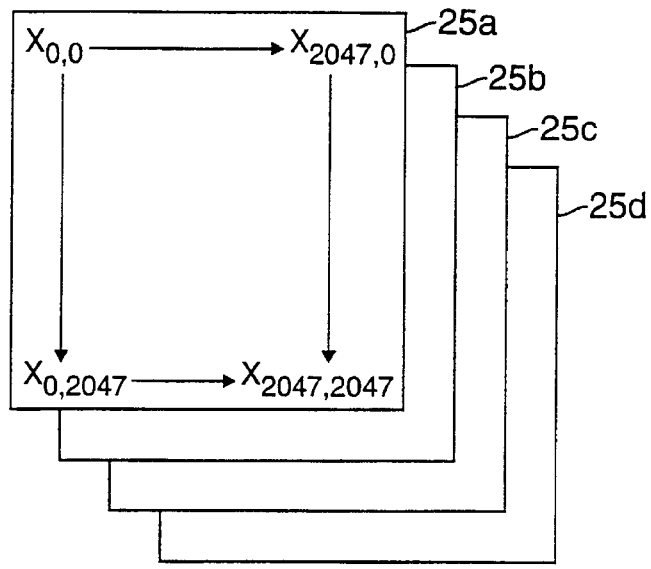
FIGS. 7A and 7B are schematic drawings showing a method by which "re-indexed" sub-images are recombined to form a single image.
Figure 7B:
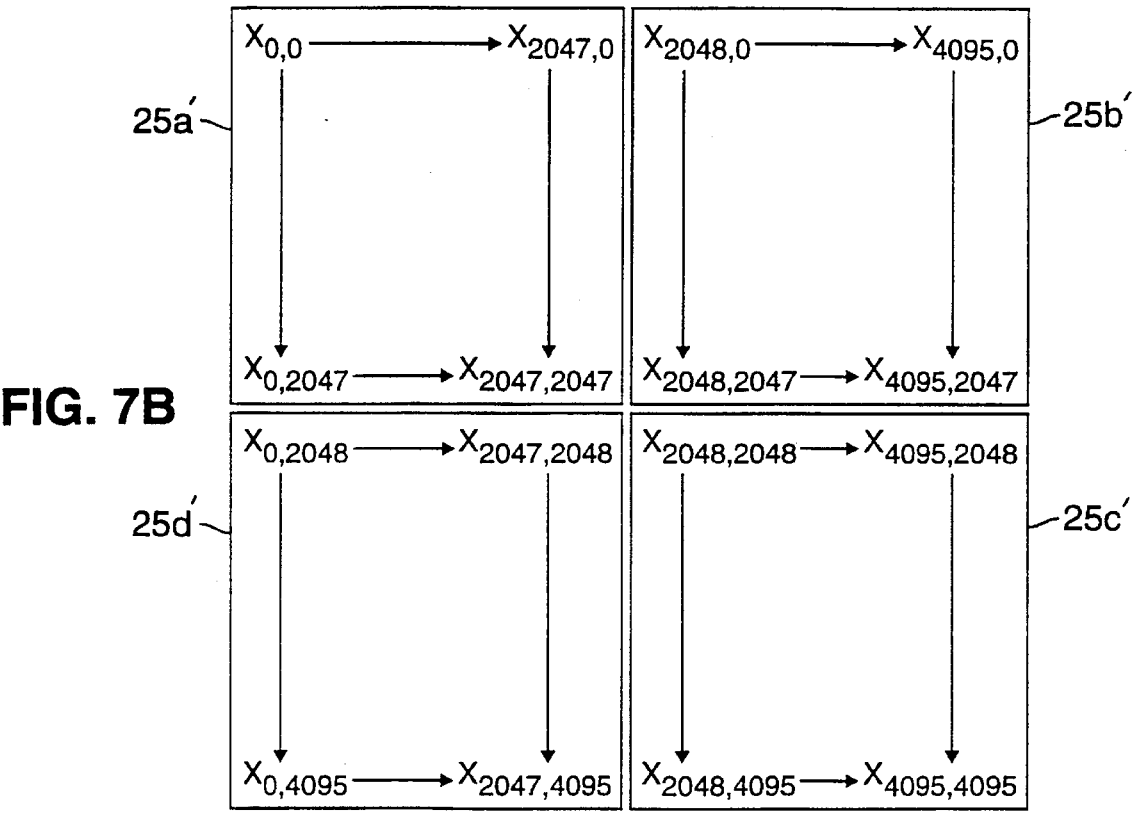

FIGS. 7A and 7B, for example, show schematically how multiple sub-images can be recombined to form a single image. In this case, multiple sub-images 25a–25d (shown in FIG. 7A) may be stored in the computer as a two-dimensional array of points, e.g., $(x_{0,0}, x_{0,1}, \ldots x_{n-1,n-1})$, where n for this case is 2048 and $x_{a,b}$ represents an element of each array. The recombination algorithm may then be used to shift each point of each array (i.e., "re-index" the array, as shown in FIG. 7B) by the same amount n so that a modified array is generated for each sub-image. In the schematic drawing shown, for example, the array of sub-image 25b' is modified to have indexing of $(x_{n-1,0}, x_{n,0}, \ldots x_{2n-1,n-1})$. The arrays of sub-images 25c' and 25d' are re-indexed in a similar manner. Once re-indexed, the arrays are such that combination of the sub-images allows a single image to be formed (this is indicated schematically by the four adjacent sub-images 25a'–25d' in FIG. 7B). Although it is not indicated in the figure, overlap between elements of the array may be used to eliminate "seams" in the image.

Figure 5:
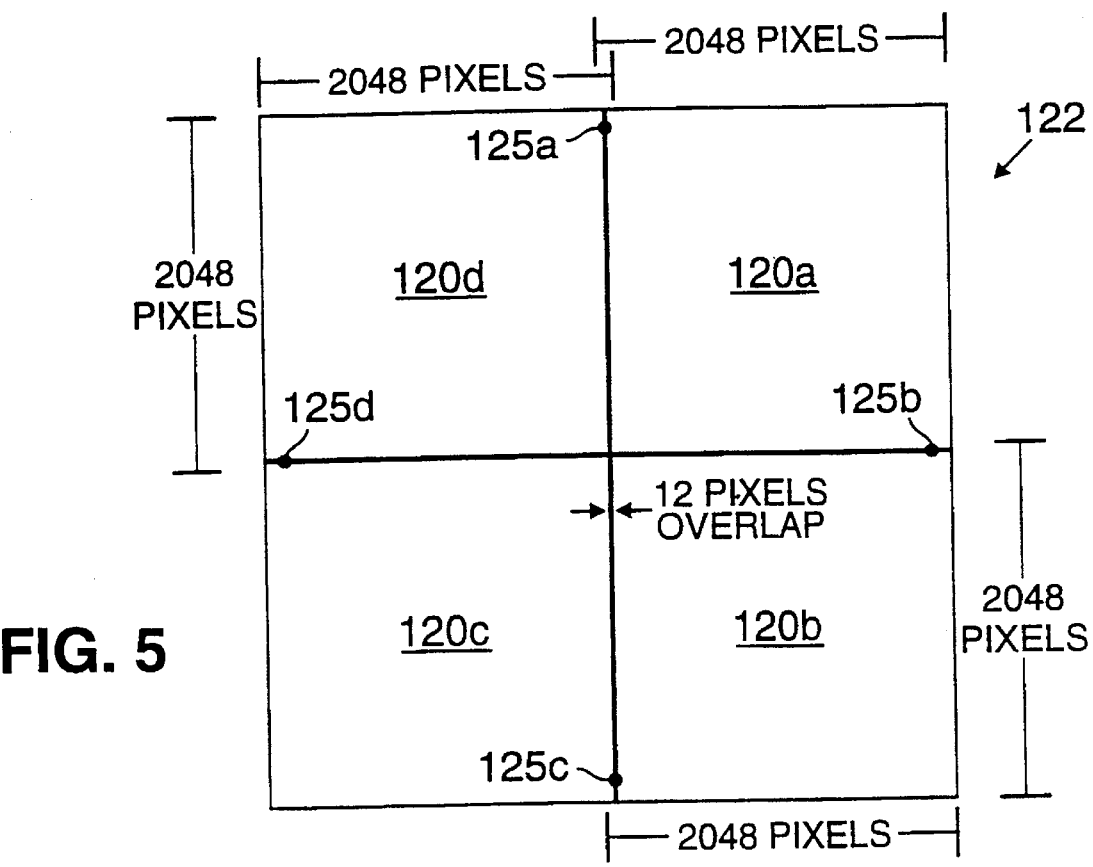
FIG. 5 is a schematic diagram showing the overlap of four sub-images generated using a scanning mirror apparatus.

FIG. 5, for example, shows how the multiple sub-images 120a–120d are recombined and partially overlapped to reconstruct the complete image. In this case, four 2048× 2048-pixel sub-images 120a–120d are generated and then recombined in a square fashion to form a complete image 122 having the same spatial resolution and approximately four times the area. To limit errors in the image reconstruction, the pixel structure of all four sub-images 120a–120d generated during the imaging process must be precisely controlled so that distorted regions, or regions of missing information, are avoided in the complete image 122. This problem is avoided in two separate ways. First, the mechanical tolerances of all mounting and filtering components, and control over the degree of rotation of the filter wheel and rotatable mirror mount, must be accurately controlled, preferably to within a displacement of better than 0.25 mm. Second, the pixel structure of each sub-image is controlled so that the inner boundaries of each digitized sub-image overlap those of the subsequent sub-image by a few pixels (e.g., 12 pixels, or about 0.58 mm, may be used as the region of overlap). In this case, the total image intensity of the pixels in the region of overlap represents the average intensity of the two overlapping pixels. Alternatively, image processing techniques known in the art may be used to eliminate any artifacts (e.g., abnormally high or low intensity values) in the regions of overlap.

Thus, when each quadrant of the object is exposed, a 2048×2048 sub-image is obtained, resulting in the generation of the four sub-images 120a–120d, each representing a different quadrant of the imaged region. During recombination, the left-most 12 pixels of the sub-images 120a and 120b are overlapped, respectively, with the right-most 12 pixels of the sub-images 120d and 120c. Similarly, the bottom-most 12 pixels of sub-images 120a and 120d are spatially overlapped, respectively, with the topmost 12 pixels of sub-images 120b and 120c. Marker pixels 125a–125d may be designated in the 12-pixel regions on the sides of each sub-image to allow for accurate overlap during the recombination procedure.

The image quality is ultimately determined by the optical detector. In addition to having high spatial resolution, it is preferred that the detector have a low-noise output and high quantum efficiency (i.e., high conversion of optical photons into electronic signals). Currently available CCDs are the preferred detectors, although other electronic imagers, such as photodiode arrays, charge-injection devices, amorphous silicon detectors, video cameras, position-sensitive detectors, photomultiplier tubes, and image intensifiers may be used as the detector of the invention. CCDs are available, for example, from Scientific Technologies, Inc.

Phosphor screens which may be used as the X-ray-to-optical converter of the invention are composed of, for example, optically transparent or semi-transparent scintillating materials, e.g., glass-based scintillating materials, $CdWO_4$, thallium-activated sodium iodide (i.e., NaI(T1)), terbium-doped glass scintillators, transparent plastic scintillators, ceramic-based scintillating materials, including $Gd_2O_3$, $Gd_2O_2S$:Pr,Ce,X, where X is F or Cl, $Gd_2O_2S$:Pr, $Y_2O_3/Gd_2O_3$, and related ceramic-based materials, e.g., as described in U.S. Pat. Nos. 4,747,973, 4,518,546, 4,473,513, and 4,525,628, and in U.S. Ser. No. 08/287,239, the contents of all of which are incorporated herein by reference. Any commercially available phosphor screen, such as those manufactured by 3M, may be used in accordance with the invention.

In all cases, the methods and apparatus of the invention are used according to standard procedures in the imaging arts. For example, in mammography or radiography, the digital imaging system may be used to replace a standard X-ray imaging system with no effect on the normal imaging procedure.

Figure 2B:
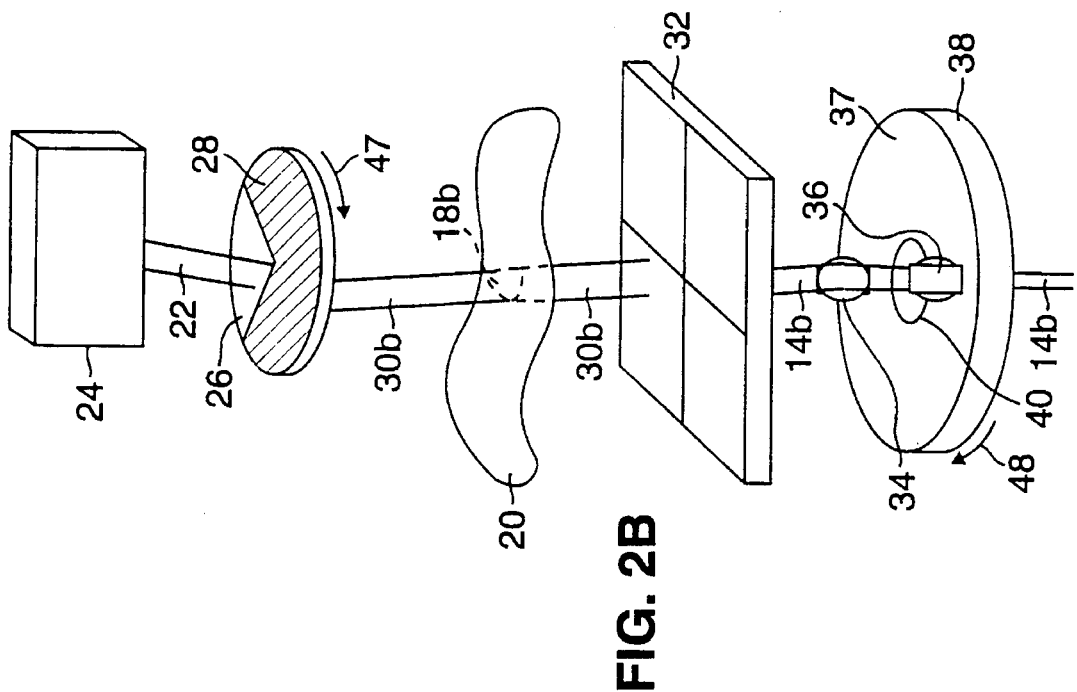
FIGS. 2A–2D are perspective views of the scanning mirror apparatus and spatial filter of FIG. 1 rotated at various stages about a central axis during the imaging process.
Figure 2A:
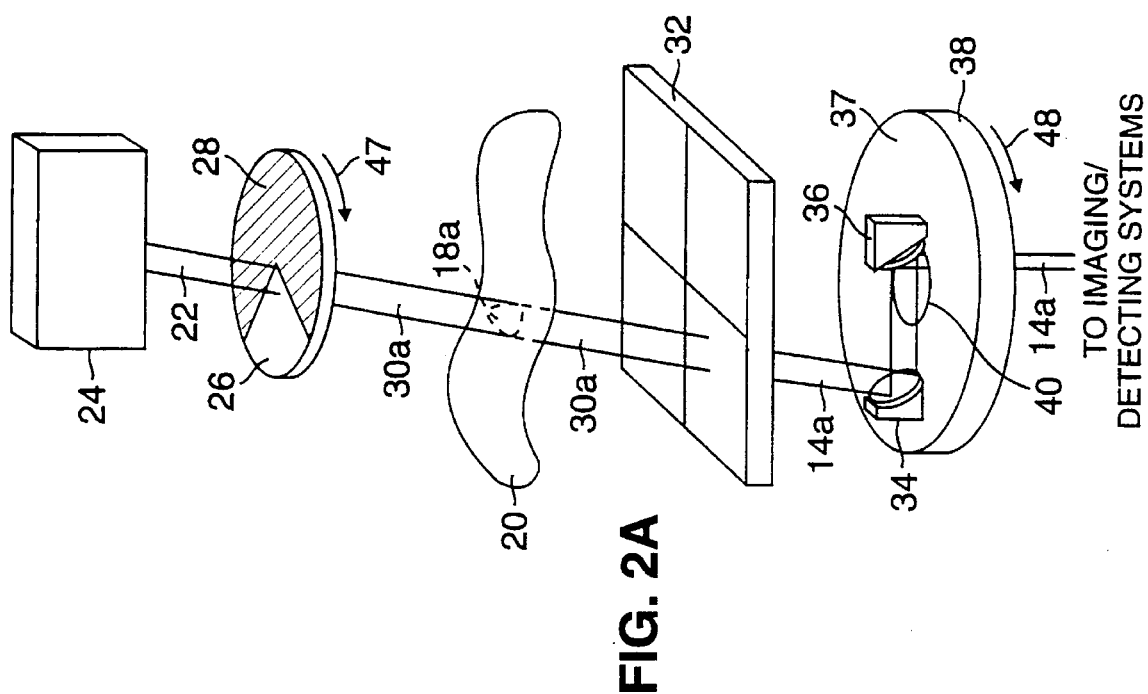

With reference now to FIGS. 2A–2D, both the filter wheel 28 and mirror mount 38 are rotated in a time-dependent fashion, and are used in conjunction with an X-ray source 24 and detector to image a region of the object 20. During imaging, generation of the optical scenes 14a–14d is accomplished by first spatially filtering the incident X-ray beam 22 to produce X-ray sub-beams 30a–30d. As is typical of X-ray sources, the incident beam 22 may have a diverging, conical spatial profile. To filter the beam, the open portion 26 of the wheel is positioned along one section of the beam 22, and the wheel is rotated about an axis centered with respect to the beam, thereby allowing transmission of multiple sub-beams during a rotational cycle. As shown in FIG. 2A, once transmitted, the X-ray sub-beam 30a irradiates a portion 18a of the object 20, resulting in a modulated X-ray beam 30a' which then impinges on a portion of the X-ray-to-optical conversion means 32 to produce the optical scene 14a. The first mounted mirror 34 is positioned to reflect the scene 14a off the surface of the second mirror 36, through the opening 40 in the rotating mount 38, and onto the imaging and detector systems.

Once the first sub-image is generated and stored in the buffer or memory of the computer, both the filter wheel 28 and mirror mount 38 are rotated 90° in the same direction, indicated as being clockwise in the figures by the arrows 47 and 48; the degree and direction of rotation may be varied depending on the size of the region to be imaged, and is the same for the filter and the mirror mount. Typically, the rotational process takes between 0.1 and 5 seconds. During rotation, the positions of the X-ray source 24, X-ray-to-optical conversion means 32, and the detector 16 remain fixed. Preferably, during rotation, both the X-ray beam and detector are blocked; this reduces exposure of the object and detector to, respectively, X-ray and optical radiation during rotation. After rotation of the spatial filter and mirror mount, the X-ray beam is filtered so that a separate sub-beam is transmitted and used to expose another portion of the object. Similarly, by moving in concert with the filtering wheel, the pair of mirrors 34, 36 are positioned to collect and steer the induced optical scene through the imaging optics and onto the detector.

Figure 2C:
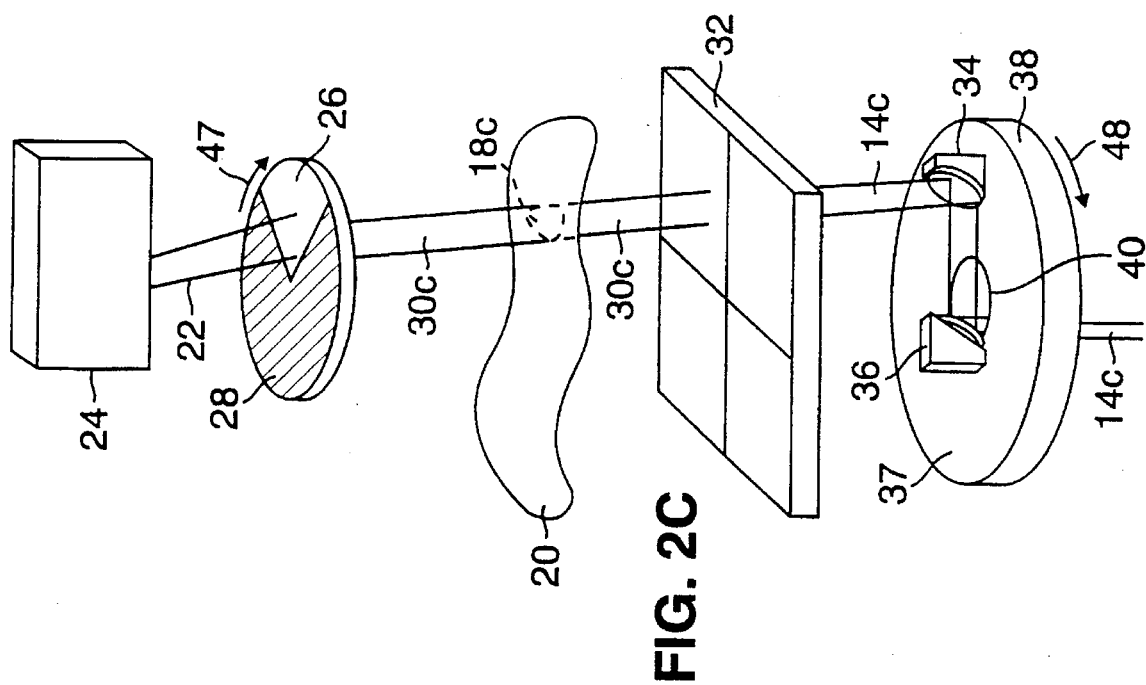
Figure 2D:
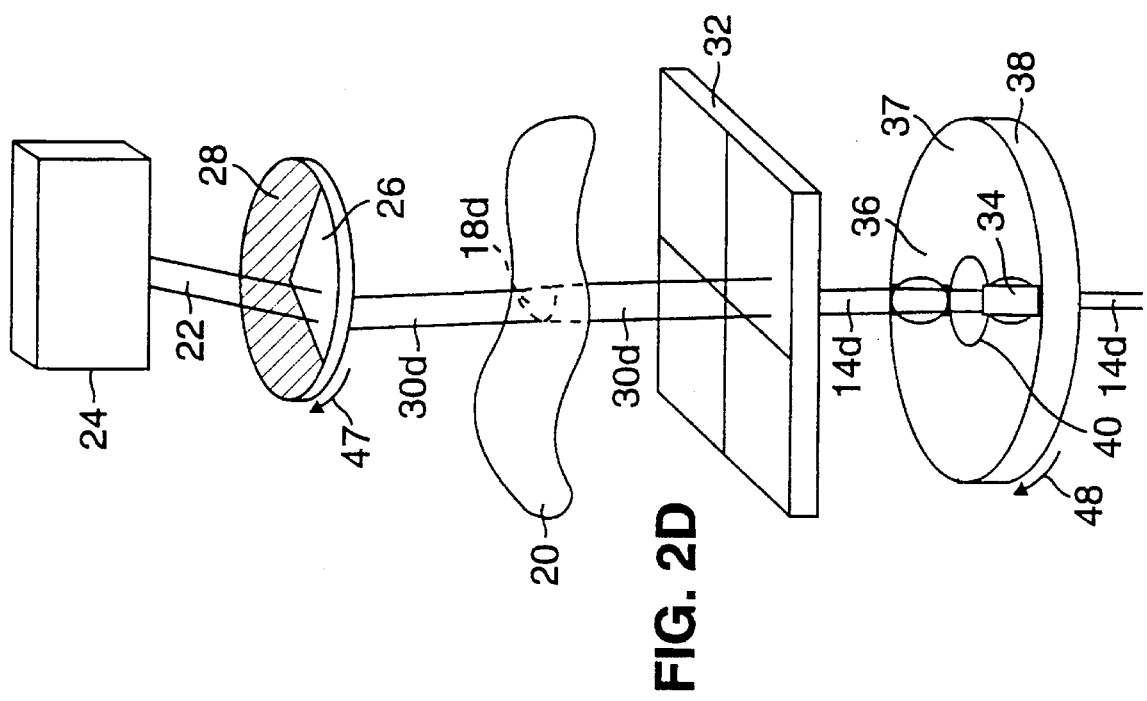

With reference now to FIG. 2B, following simultaneous rotation of the filter wheel 28 and rotating mount 38, a spatially separate sub-beam 30b is generated and used to irradiate a new portion 18b of the object 20, thereby producing a modulated beam 30b' which impinges a second portion of the X-ray-to-optical conversion means 32 to generate a new optical scene 14b. The scene is then collected by the newly positioned mirror pair 34, 36, where it is steered onto the imaging and detecting systems to generate and store a sub-image representative of the region 18b. Once the sub-image is digitized and stored, the process of rotating the filter wheel and rotatable mount is repeated, as shown in FIGS. 2C and 2D, to generate and store sub-images of separate regions 18c, 18d of the object. Once collected and stored, each digitized sub-image is adjusted (i.e., the pixels may be shifted) and then combined using image-combining computer algorithms to form the complete image of the region.

Figure 3:
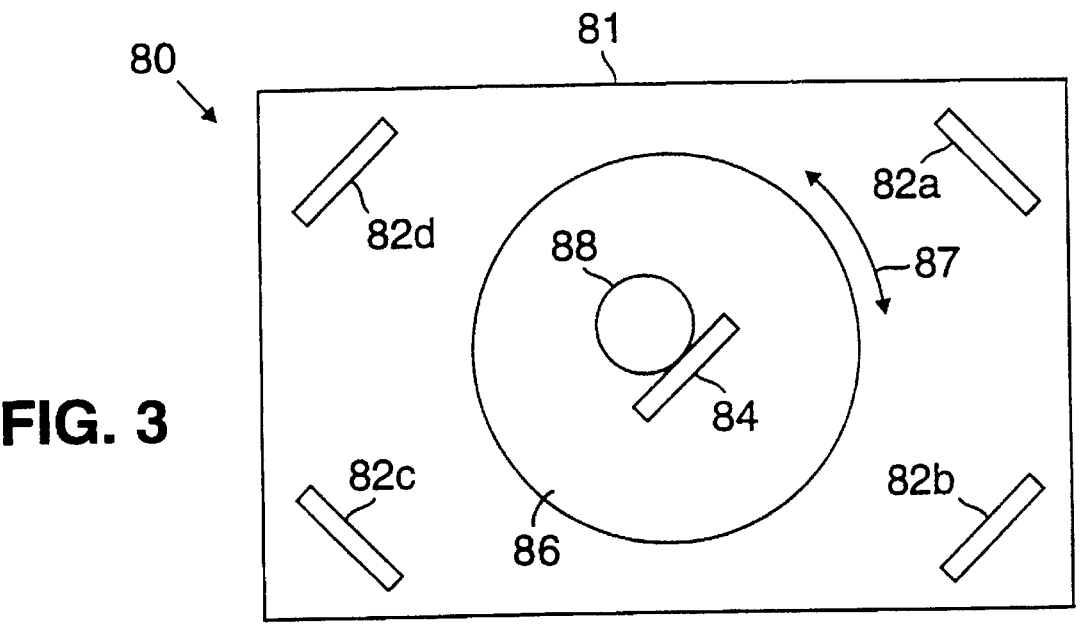
FIG. 3 is a top view of the optical configuration of the scanning mirror apparatus according to an alternate embodiment of the invention.

Although the embodiments shown in FIGS. 1 and 2A–2D show a scanning mirror apparatus wherein both the first 34 and second 36 mirrors are rotated, other methods for achieving multiple sub-images are also within the scope of the invention. For example, with reference now to FIG. 3, scanning mirror apparatus 80 may include a single rotating mirror 84 surrounded by four (or more) stationary mirrors 82a–82d mounted on a stage 81. Each of the stationary mirrors is positioned to receive the emitted optical scenes representative of the portions, e.g., four quadrants, of the region to be imaged. The rotating mirror 84 is mounted on a rotating stage 86 and is configured to rotate about a central axis aligned with the center of the filter wheel and the region to be imaged. In this case, an emitted scene is reflected off one of the stationary mirrors and onto the rotating mirror 84, where it is then reflected through an opening 88 and steered through the imaging system and onto the detector. Once a sub-image is collected, the stage 86 is rotated (as indicated by the arrow 87) to direct a scene reflected off a neighboring stationary mirror onto the detector. This process is repeated until all desired sub-images are collected.

In still other embodiments, all reflecting mirrors are stationary, and the detector is mounted on a stage configured to translate and detect each of the emitted optical scenes. In addition, it is understood that in all cases, more or less than four optical scenes (and corresponding sub-images) may be collected and used to form the complete image. In general, this is achieved by reducing the degree of rotation of both the filter wheel and mirror mount about the central axis.

In all cases, the mirrors used to reflect the optical scenes are coated with materials, such as standard dielectric stack coatings or reflective metal coatings, having a high reflectivity matched to the emission spectrum of the luminescing screen. Typically, this region is in the range of about 500–550 nm. All optics should be chosen to minimize distortion of the wavefronts of each optical scene. Reflecting prisms, or partially transmitting beam-splitting optics may be used as alternatives to mirrors.

Figure 4:
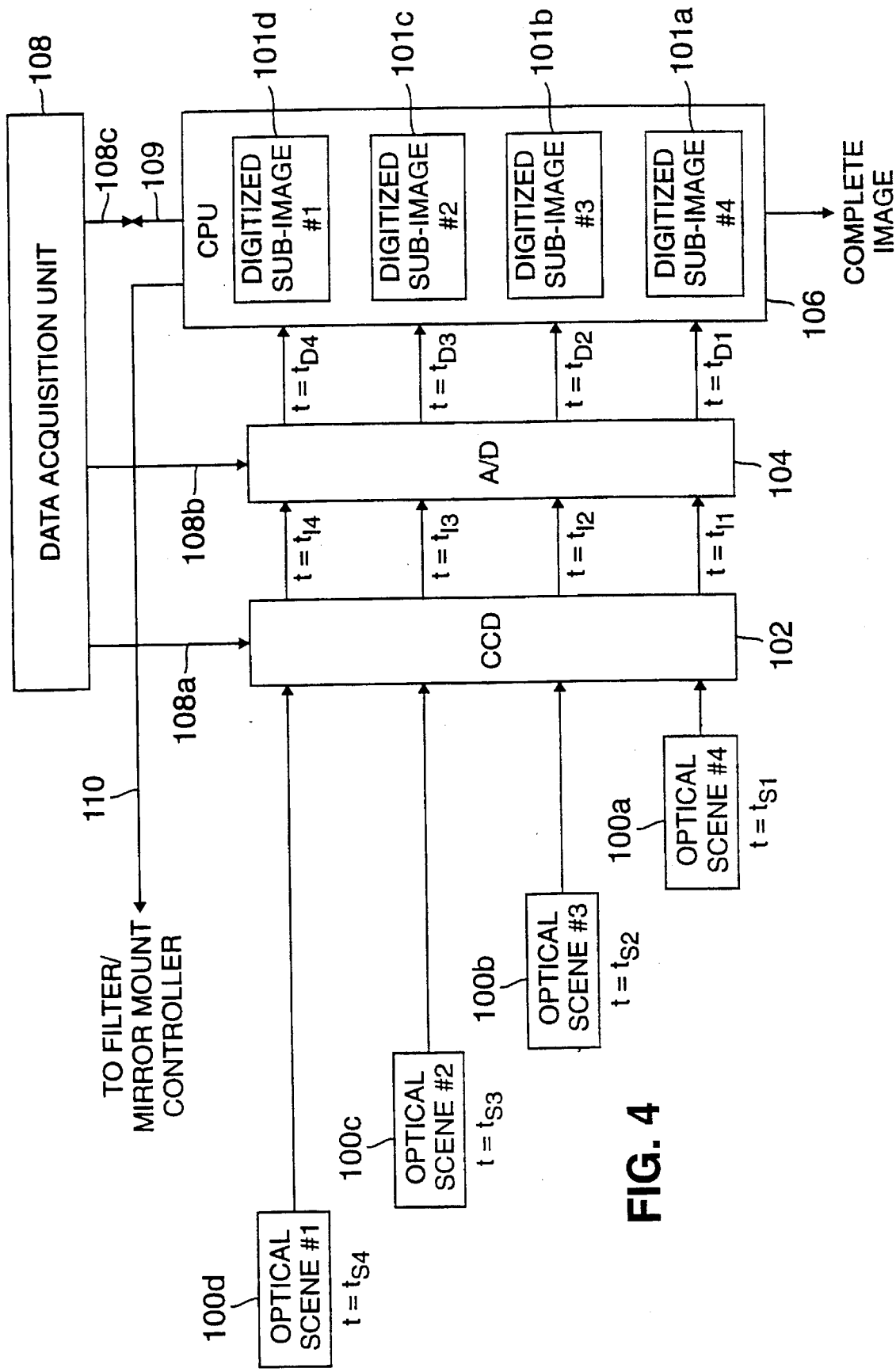
FIG. 4 is a schematic diagram of the processes used to detect and combine sub-images generated using the scanning mirror apparatus.

Referring now to FIG. 4, optical scenes 100a–100d are detected at times $t=t_{s1}$ through $t=t_{s4}$ by the CCD 102 to generate a complete image. The CCD is preferably a commercially available, high-end imager containing an array of 2048×2048 pixels, with each pixel having an area of about 24 μm×24 μm. The time interval Δt between detection of subsequent scenes, i.e. $\Delta t = t_{si} - t_{si+1}$ where i may be, for example, between 1 and 3, is limited by the rate at which the CCD can transmit data to an analog-to-digital (A/D) converter 104. This rate is typically between a few hundred KHz to about 5 MHz. For example, a CCD having a 2048×2048-pixel array at 2 bytes/pixel and operating near 4 MHz requires about 1 second to output a sub-image to the A/D converter. CCDs operating at higher frequencies can be read out at faster rates, thereby expediting the image collecting process. During the data collection time period, the CCD 102 is typically left in an integration mode, thereby allowing the optical scene to be continuously collected and averaged. In addition, the CCD is typically cooled to limit thermal effects which may decrease the signal-to-noise ratio of the detected sub-image. A non-cooled CCD may be used if the pixel readout rate is sufficiently fast to prevent thermal current build-up.

Once generated, the electronic images representative of the detected scenes are sequentially sent to the A/D converter 104 at times $t=t_{I1}$ through $t=t_{I4}$. The amplitude of the analog signal for each pixel corresponds to the magnitude of the optical intensity at the pixel, and the collective response of the array represents the total sub-image to be digitized. The light-induced electronic images are then digitized and sequentially transported at times $t=t_{D1}$ through $t=t_{D4}$ to the CPU 106, where they are stored in memory as digitized sub-images 101a–101d.

The timing of the conversion of the optical scenes 100a–100d to the digital sub-images 101a–101d is controlled by a standard data acquisition unit 108 (available, for example, from National Instruments) contained within the computer. The data acquisition unit 108 sends time-dependent control signals 108a–108c to the CCD 102, A/D converter 104, and CPU 106, and additionally receives status signals from the CPU indicating when a digitized sub-image has been registered in memory. At this point, the CPU also sends out a control signal 110 which is received by a controller driving the rotation of the spatial filter and mirror mount, thereby allowing subsequent optical scenes representative of separate portions of the object to be generated. Although not shown in FIG. 4, it is understood that current amplifiers and pre-amplifiers may be used in combination with the CCD in order to amplify the output analog signal.

The CCD used in accordance with the present invention preferably includes (i) a large optically active area; (ii) high spatial resolution (i.e., small pixel size); and, (iii) high total quantum gain (i.e., high quantum efficiency at the emission peak of the X-ray-to-optical conversion screen). Any currently available CCD may be used as the optical detector. These devices typically can be read in both serial and parallel modes at rates between about 50 KHz and 10 MHz, and have quantum efficiencies ranging from approximately 30% to 80%, depending on the device and manufacturer.

During the imaging procedure, the optical scene may be demagnified on the face of the CCD in order to increase the field of coverage of the imaging system. Preferably, the optical scene is imaged onto the CCD with a size ratio in the range of 1:1 (no demagnification) to 2:1 (50% demagnification). To maximize the intensity of the image, the imaging lens must have a high optical coupling efficiency at the wavelength of the emitted scene. In the radiographic application, for example, the F-number may be approximately F/1, and is typically between F/0.7 to F/1.4, although this is not an absolute requirement. If an image intensifier is to be used, the F-number may be significantly higher, thereby allowing for an even smaller lens aperture.

Other criteria which may affect the optical coupling efficiency of the lens include optical transparency at the central wavelength of the emitted scene, optical properties of the anti-reflection coatings, purity of the glass used to fabricate the lens, and the degree of aberration in the lens. The lens used in the imaging system is preferably designed for close imaging, rather than for infinite object distances. To this effect, air-spaced astigmatic lenses may be used in the imaging system. Similarly, to reduce vignetting effects, the lens used in the imaging system preferably has a large effective diameter, and may be artificially flattened on a single side.

In alternate embodiments, the present invention allows imaging of regions other than those which can be divided into four quadrants. For example, by modifying the spatial filtering device to translate linearly with respect to the spatial profile of the X-ray beam, X-ray sub-beams can be generated and used to sequentially irradiate, for example, an elongated region of tissue. In this case, the scanning mirror apparatus is configured to linearly translate in order to collect optical scenes induced by the linearly configured sub-beams, and then steer those beams into the CCD. As before, the optical scenes are then detected and digitized, and then combined in a linear fashion to form the complete image of the elongated region. Regions having unconventional shapes and sizes can be imaged in a similar fashion.

Figure 6:
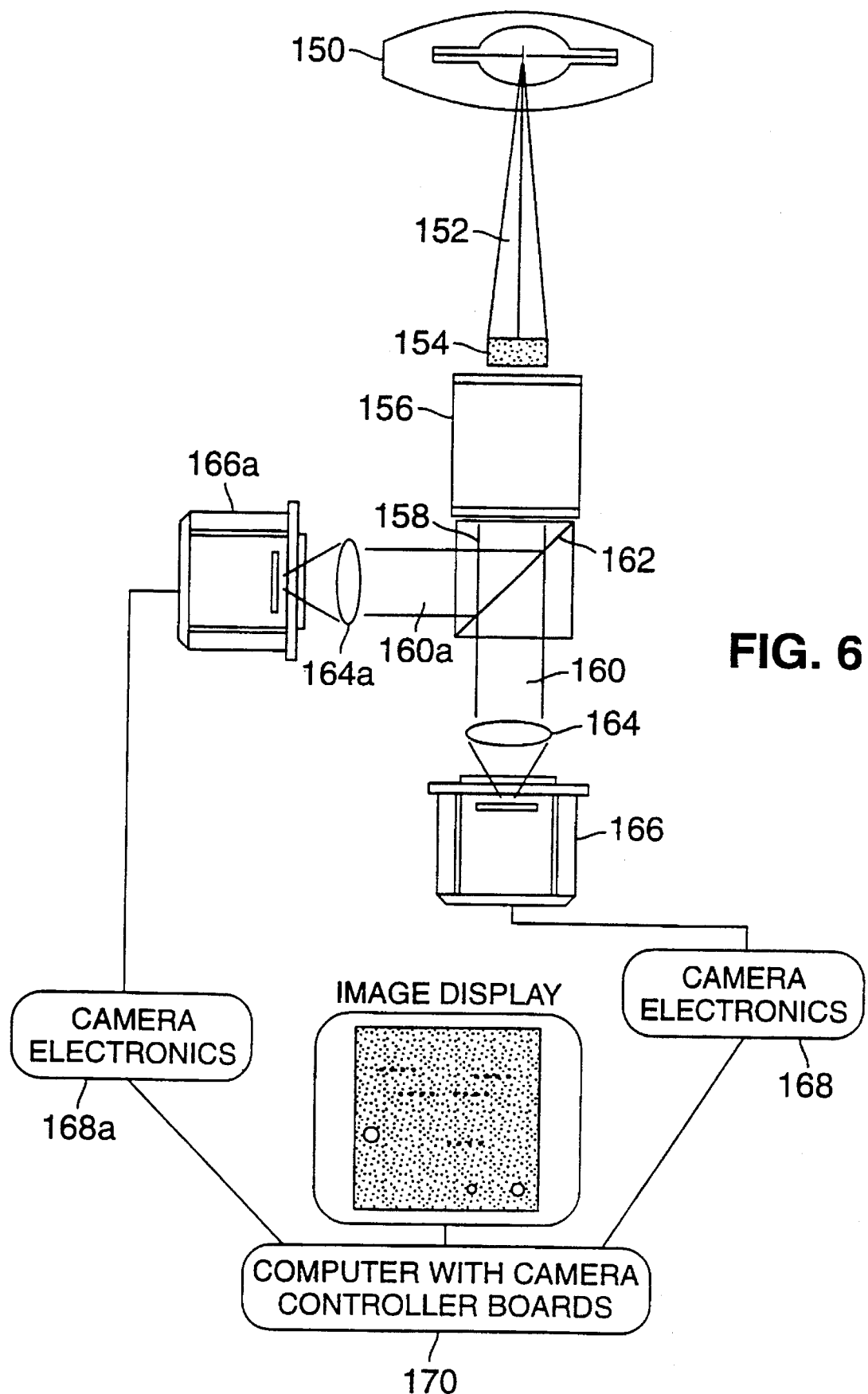
FIG. 6 is a schematic top view of a two-CCD detector embodiment of the invention.

In still other embodiments, a single scene can be optically separated into multiple components, with each component being monitored with a separate detector. This allows formation of a small-scale image having spatial resolution which is twice that of a conventional image. Referring now to FIG. 6, in such an embodiment, an X-ray source 150 generating an X-ray beam 152 is used to irradiate an object 154. The modulated X-ray beam then passes through a conventional image intensifier 156 to generate a single optical scene 158, which is split into scenes 160, 160a using a beam-splitter 162 (e.g., a pelical beam-splitter). Each scene is then imaged using imaging systems 164, 164a (e.g., single lenses) onto detectors 166, 166a (e.g., CCDs), resulting in the generation of two separate electronic images which can then be digitized using electronic means 168, 168a and stored in a computer 170. Each detector 166, 166a is spatially offset relative to each other by a distance equal to a fraction of a single pixel, resulting in the generation of digital images which are correspondingly offset. The offset digital images are then computationally recombined to form a small-scale, high-resolution digital image.

In this embodiment, because the optical scene is split into two or more lower-intensity components, it may be necessary to use a high-gain image intensifier as shown in the figure, although this device is not essential. Alternatively, a fast X-ray screen may be used for X-ray-to-optical conversion.

Other Embodiments

Other embodiments are within the scope of the following claims. For example, the methods of the invention may be used for imaging applications not associated with radiography or mammography; other applications include large-scale image production in cinematography, or applications relating to conventional and confocal microscopy.

What is claimed is:

1. A method for generating a large-field, high-resolution image of an object, said method comprising the steps of:

(a) generating a first optical scene representative of a first portion of the object by:
    spatially filtering a first portion of an incident X-ray field with a spatial filter to generate a first, two-dimensional X-ray sub-field;
    projecting the first X-ray sub-field through the first portion of the object and then through an X-ray-to-optical conversion screen to produce the first optical scene; and,
    directing the first optical scene with a reflecting assembly onto an optical detector to generate a two-dimensional sub-image of the first portion of the object;

(b) rotating both the spatial filter and the reflecting assembly;

(c) generating a second optical scene representative of a second portion of the object by:
    spatially filtering a second portion of the incident X-ray field with the rotated spatial filter to generate a second, two-dimensional X-ray sub-field;
    projecting the second x-ray sub-field through the second portion of the object and then through the X-ray-to-optical conversion screen to produce the second, optical scene; and,
    directing the second optical scene with the rotated reflecting assembly onto the optical detector to generate a two-dimensional sub-image of the second portion of the object; and, (d) combining all two-dimensional sub-images to form a large-field, high-resolution image of the object.

2. A method of claim 1, wherein following step (c) and prior to step (d), the method further comprises the steps of repeating steps (b) and (c) for a third optical scene representative of a third portion of the object to generate a two-dimensional sub-image of the third portion of the object.

3. The method of claim 2, wherein the optical detector comprises a two-dimensional optically active region having about the same area as one of the two-dimensional optical scenes.

4. A method of claim 1, wherein the reflecting assembly comprises a mirror positioned to reflect the optical scene onto said optical detector.

5. A method of claim 1, wherein the reflecting assembly comprises a first and second mirror, with the first mirror configured to receive and reflect the optical scene off the second mirror and onto the optical detector.

6. A method of claim 1, wherein the reflecting assembly comprises a single mirror positioned to reflect the optical scene onto the optical detector.

7. A method of claim 1, wherein each optical scene is a two-dimensional optical scene directed onto the optical detector with an imaging system.

8. A method of claim 1, wherein the step of spatial filtering comprises positioning an opening of a spatial filter along the portion of the incident X-ray field, thereby producing an X-ray field having a reduced spatial profile.

9. A method of claim 1, where between steps (a) and (b), the spatial filter and mirror assembly are simultaneously rotated about 90° along the same central axis.

10. A method of claim 1, wherein said step (c) is performed with a computer algorithm which performs the steps of:
    adjusting said two-dimensional array of points of each sub-image so that, when combined, each sub-image is representative of a separate portion of said object, and
    combining said adjusted two-dimensional arrays of points to form the resultant image of said object.

11. The method of claim 1, wherein during said combining step (d), the first and second two-dimensional sub-images are overlapped to be off-set relative to one another, said overlapped, off-set sub-images forming the large-field, high-resolution image of the object.

12. An apparatus for generating a large-field, high-resolution image of an object, said apparatus comprising:

an X-ray imaging system for generating at least two, two-dimensional optical scenes representative of at least two spatially separate portions of the object;

an optical detector;

a rotating and reflecting assembly comprising at least one reflecting optic, said assembly configured to sequentially receive and then direct the two-dimensional optical scenes onto said optical detector to generate a two-dimensional sub-image for each optical scene; and, electronics that combine the two-dimensional sub-images together to at least partially form the large-field, high-resolution image of the object.

13. An apparatus of claim 12, wherein said reflecting assembly comprises a first and second mirror, with the first mirror mounted and angled to receive the optical scene and then reflect the optical scene off the second mirror and onto the optical detector.

14. An apparatus of claim 12, wherein said reflecting assembly comprises a first mirror positioned to receive and then reflect the optical scene onto said optical detector.

15. An apparatus of claim 12, wherein said reflecting assembly comprises a prism positioned to receive and then reflect the optical scene onto said optical detector.

16. An apparatus of claim 12, wherein said reflecting assembly further comprises rotating means for rotating said assembly.

17. An apparatus of claim 16, wherein said rotating means comprises a rotatable mount having a circular cross section and configured to rotate said assembly radially about a central axis to sequentially direct each two-dimensional optical scene onto said optical detector.

18. An apparatus of claim 12, wherein said optical detector is a CCD.

19. An apparatus of claim 12, wherein said X-ray imaging system comprises:

means for generating an incident X-ray field;

a spatial filter for spatially filtering a portion of said incident X-ray field to generate a first, two-dimensional X-ray sub-field, said first X-ray sub-field being projected through a first portion of the object to produce a first modulated X-ray sub-field;

means for rotating said spatial filter to generate additional two-dimensional X-ray sub-fields; and, an X-ray-to-optical conversion screen configured to receive each modulated X-ray sub-field and then generate a two dimensional X-ray-induced optical scene representative of said portion of said object.

20. An apparatus of claim 19, wherein said spatial filter comprises an X-ray attenuating material and an opening configured to spatially filter the incident X-ray field.

* * * * *